(12) United States Patent
Carroll

(10) Patent No.: US 11,207,534 B2
(45) Date of Patent: Dec. 28, 2021

(54) ALWAYS ON RECEIVER WITH OFFSET CORRECTION FOR IMPLANT TO IMPLANT COMMUNICATION IN AN IMPLANTABLE MEDICAL SYSTEM

(71) Applicant: Pacesetter, Inc., Sylmar, CA (US)

(72) Inventor: Kenneth J. Carroll, Los Altos, CA (US)

(73) Assignee: Pacesetter, Inc., Sylmar, CA (US)

( * ) Notice: Subject to any disclaimer, the term of this patent is extended or adjusted under 35 U.S.C. 154(b) by 23 days.

(21) Appl. No.: 16/684,270

(22) Filed: Nov. 14, 2019

(65) Prior Publication Data

US 2020/0078595 A1 Mar. 12, 2020

Related U.S. Application Data

(62) Division of application No. 15/605,756, filed on May 25, 2017, now Pat. No. 10,722,724.

(51) Int. Cl.
*A61N 1/378* (2006.01)
*A61N 1/372* (2006.01)
(Continued)

(52) U.S. Cl.
CPC .............. *A61N 1/378* (2013.01); *A61N 1/056* (2013.01); *A61N 1/0587* (2013.01);
(Continued)

(58) Field of Classification Search
CPC ...... A61N 1/378; A61N 1/056; A61N 1/0587; A61N 1/3704; A61N 1/3708;
(Continued)

(56) References Cited

U.S. PATENT DOCUMENTS

| 4,390,020 A | 6/1983 | Herpers |
| 5,350,412 A | 9/1994 | Hoegnelid et al. |

(Continued)

FOREIGN PATENT DOCUMENTS

| CN | 102901902 A | 1/2013 |
| CN | 104716914 A | 6/2015 |

(Continued)

OTHER PUBLICATIONS

Restriction Requirement dated Oct. 2, 2018, U.S. Appl. No. 15/605,756, filed May 25, 2017.

(Continued)

*Primary Examiner* — Niketa Patel
*Assistant Examiner* — Minh Duc G Pham
(74) *Attorney, Agent, or Firm* — Vierra Magen Marcus LLP

(57) ABSTRACT

Disclosed herein are implantable medical devices (IMDs) including a receiver and a battery, and methods for use therewith. The receiver includes first and second differential amplifiers, each of which monitors for a predetermined signal within a frequency range and drains power from the battery while enabled, and while not enabled drains substantially no power from the battery. To remove undesirable input offset voltages, each of the differential amplifiers, while enabled, is selectively put into an offset correction phase during which time the predetermined signal is not detectable by the differential amplifier. At any given time at least one of the first and second differential amplifiers is enabled without being in the offset correction phase so that at least one of the differential amplifiers is always monitoring for the predetermined signal. In this manner, the receiver is never blind to signals, including the predetermined signals, sent by another IMD.

20 Claims, 7 Drawing Sheets

(51) Int. Cl.
  *H04B 13/00* (2006.01)
  *A61N 1/05* (2006.01)
  *A61N 1/37* (2006.01)
  *A61N 1/375* (2006.01)
  *A61N 1/39* (2006.01)
  *H03F 3/38* (2006.01)
  *H03F 3/45* (2006.01)

(52) U.S. Cl.
  CPC ......... *A61N 1/3704* (2013.01); *A61N 1/3708* (2013.01); *A61N 1/3756* (2013.01); *A61N 1/37205* (2013.01); *A61N 1/37223* (2013.01); *A61N 1/37235* (2013.01); *A61N 1/37288* (2013.01); *A61N 1/3962* (2013.01); *H03F 3/38* (2013.01); *H03F 3/45* (2013.01); *H04B 13/005* (2013.01); *A61N 2001/0585* (2013.01); *H03F 2200/375* (2013.01)

(58) Field of Classification Search
  CPC ............ A61N 1/37205; A61N 1/37223; A61N 1/37235; A61N 1/37288; A61N 1/3756; H03F 3/38; H03F 3/45
  See application file for complete search history.

(56) References Cited

U.S. PATENT DOCUMENTS

| | | | |
|---|---|---|---|
| 5,713,934 A | | 2/1998 | Leckrone |
| 2016/0121129 A1* | | 5/2016 | Persson ................ A61N 1/3756 607/32 |
| 2016/0294331 A1* | | 10/2016 | Ivanov ...................... H03F 1/26 |
| 2017/0230018 A1 | | 8/2017 | Hwang |
| 2018/0339160 A1 | | 11/2018 | Carroll |

FOREIGN PATENT DOCUMENTS

| | | |
|---|---|---|
| CN | 105099474 A | 11/2015 |
| CN | 105979655 A | 9/2016 |
| JP | 2014-530713 | 11/2014 |
| JP | 2015-503397 | 2/2015 |
| WO | WO2005/067563 A2 | 7/2005 |
| WO | WO2011/047271 A1 | 4/2011 |
| WO | WO2012/101467 A1 | 8/2012 |

OTHER PUBLICATIONS

Response to Restriction Requirement dated Oct. 9, 2018, U.S. Appl. No. 15/605,756, filed May 25, 2017.
Non-final Office Action dated Mar. 22, 2019, U.S. Appl. No. 15/605,756, filed May 25, 2017.
Response to Office Action dated Jul. 22, 2019, U.S. Appl. No. 15/605,756, filed May 25, 2017.
Notice of Allowance dated Nov. 7, 2019, U.S. Appl. No. 15/605,756, filed May 25, 2017.
International Search Report & The Written Opinion of the International Searching Authority dated Jul. 9, 2018, International Application No. PCT/US2018/028392.
English Abstract of CN Publication No. 105099474 published Nov. 25, 2015.
English Abstract of CN Publication No. 104716914 published Jun. 17, 2015.
English Abstract of CN Publication No. 102901902 published Jan. 30, 2013.
English Abstract of CN Publication No. 105979655 published Sep. 28, 2016.
Office Action dated Dec. 3, 2020, Chinese Patent Application No. 201880025389.1.
Office Action dated Jan. 5, 2021, Japanese Patent Application No. 2019-564081.
Response to Office Action dated Mar. 30, 2021, Japanese Patent Application No. 2019-564081.
English Abstract of JP Publication No. 2014-530713 published Nov. 20, 2014.
English Abstract of JP Publication No. 2015-503397 published Feb. 2, 2015.

* cited by examiner

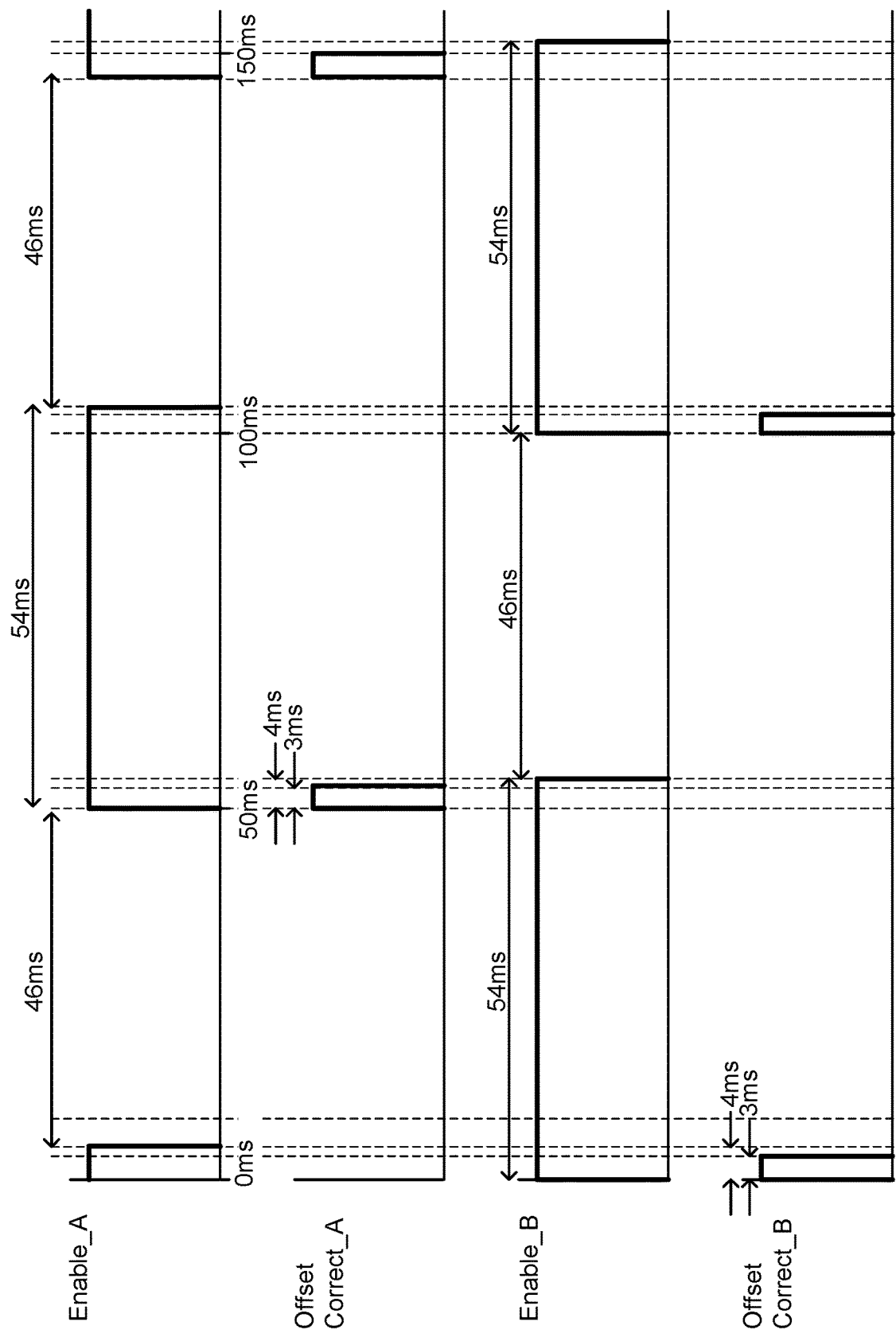

ALWAYS ON RECEIVER WITH OFFSET CORRECTION FOR IMPLANT TO IMPLANT COMMUNICATION IN AN IMPLANTABLE MEDICAL SYSTEM

PRIORITY CLAIM

This application is a Divisional of and claims priority to U.S. patent application Ser. No. 15/605,756, filed May 25, 2017, which was published as U.S. Patent Application Publication No. 2018/033916 on Nov. 29, 2018, and issued as U.S. Pat. No. 10,722,724 on Jul. 28, 2020, which is incorporated herein by reference.

FIELD OF TECHNOLOGY

Embodiments described herein generally relate to methods and systems for communication between implantable medical devices.

BACKGROUND

Implantable medical devices and systems often rely on proper communications to operate correctly. For example, in a dual chamber pacemaker system, implant-to-implant (i2i) communications are critical for proper synchronization and operation of the system. Such a system can utilize conductive communication, whereby i2i communication signals are received and transmitted using the same electrodes that are used for sensing and/or delivery of pacing therapy. Where conductive communication is utilized for i2i communication, a received signal is likely to have a low amplitude, e.g., be under 1 mV in amplitude. Accordingly, in such a system the use of a traditional differential amplifier as a receiver is not useful as the input offset voltage of a traditional differential amplifier will typically be greater than 1 mV, e.g., likely 10 mV or more with additional variation over time and temperature. Additionally, a traditional differential amplifier is very susceptible to input offset voltage drift, which is undesirable when attempting to detect low amplitude i2i signals.

SUMMARY

Implantable medical devices (IMDs), and methods for use therewith, are described herein. Such an IMD can be a leadless pacemaker (LP) configured to be implanted within or on a wall of an atrial or ventricular chamber, but is not limited thereto.

In accordance with certain embodiments, an IMD includes, inter alia, a receiver and a battery. The receiver includes first and second differential amplifiers, each of which is selectively enabled, each of which includes differential inputs, and each of which includes an output. The battery powers electrical components of the IMD, including the first and second differential amplifiers, while the electrical components are enabled. Each of the first and second differential amplifiers, while enabled, is configured to monitor for a predetermined signal within a frequency range. The predetermined signal can be, e.g., a wakeup signal within a frequency range. More specifically, the wakeup signal can be a low frequency wakeup pulse within a low frequency range, e.g., from 1 kHz to 100 kHz. Each of the first and second differential amplifiers, while enabled, drains current and thereby power from the battery. By contrast, each of the first and second differential amplifiers, while not enabled, drains substantially no current and thus substantially no power from the battery. Substantially no current and substantially no power, as the phrases are used herein, mean respectively at least 100× less current and at least 100× less power than is consumed by a differential amplifier when it is enabled. In order to remove undesirable input offset voltages due, e.g., to input offset voltage drift, each of the first and second differential amplifiers, while enabled, is capable of being selectively put into an offset correction phase during which time the predetermined signal (e.g., a wakeup pulse) is not detectable by the differential amplifier. In accordance with certain embodiments of the present technology, at any given time at least one of the first and second differential amplifiers of the receiver is enabled without being in the offset correction phase so that at least one of the first and second differential amplifiers is always monitoring for the predetermined signal within the frequency range. In this manner, the receiver is never blind to messages, including wakeup signals, sent by another IMD, such as another LP.

In accordance with specific embodiments of the present technology, the first and second differential amplifiers are simultaneously enabled for less than 20% of a time that only one of the first and second differential amplifiers is enabled. Additionally, one of the first and second differential amplifiers is in the offset correction phase for at least a majority of a time that the first and second differential amplifiers are simultaneously enabled. To further save battery power, in accordance with specific embodiments of the present technology, the first and second differential amplifiers are simultaneously enabled for less than 10% the time that only one of the first and second differential amplifiers is enabled.

In accordance with specific embodiments of the present technology, the IMD also includes first and second electrodes that are coupled to the differential inputs of each of the first and second differential amplifiers. In this manner, the electrodes can be used for receiving implant-to-implant (i2i) communication signals. The electrodes can also be used for transmitting i2i communication signals. The same electrodes can also be used for delivering cardiac stimulation pulses, as well as for sensing intrinsic or evoked cardiac activity.

In accordance with specific embodiments of the present technology, the receiver including the first and second differential amplifiers is a first receiver, and the IMD also includes a second receiver that is nominally kept in a disabled state when not being used, in order to conserver power. In such embodiments, the predetermined signal that each of the first and second differential amplifiers of the first receiver is configured to monitor for can be a wakeup signal (e.g., a wakeup pulse) within a first frequency range (e.g., from 1 kHz to 100 kHz). The second receiver, which is also coupled to the first and second electrodes, is selectively enabled in response to one of the first and second differential amplifiers of the first receiver detecting the wakeup signal within the first frequency range. The second receiver is configured to receive one or more i2i communication signals within a second frequency range that is higher than the first frequency range while the second receiver is enabled. The second receiver consumes more power than the first receiver while the second receiver is enabled, and thus, it is beneficial to keep the second receiver disabled except when it is needed. In accordance with specific embodiments of the present technology, the IMD includes OR gate circuitry having inputs coupled to the outputs of the first and second differential amplifiers of the first receiver and having an output coupled to an enable terminal of the second receiver.

Pulse conditioning circuitry is optionally coupled between the output of the OR gate circuitry and the enable terminal of the second receiver.

In accordance with specific embodiments of the present technology, the IMD is a leadless pacemaker (LP) including a hermetic housing that supports the first and second electrodes and within which the first and second receivers and the battery are disposed.

In accordance with specific embodiments of the present technology, while the first differential amplifier is enabled and in the offset correction phase, the second differential amplifier is enabled without being in the offset correction phase. Conversely, while the second differential amplifier is enabled and in the offset correction phase, the first differential amplifier is enabled without being in the offset correction phase. This way at least one of the first and second differential amplifiers is always enabled without being in the offset correction phase, and thus, is always capable of monitoring for and detecting the predetermined signal (e.g., the wakeup signal). This is why the receiver that includes the first and second differential amplifiers can be said to always be on.

In accordance with specific embodiments of the present technology, each of the first and second differential amplifiers is an auto-zero differential amplifier, and the offset correction phase is an auto-zero phase. Alternatively, each of the first and second differential amplifiers can be a chopper-stabilized differential amplifier, in which case the offset correction phase is a chopper-stabilization phase. Other variations are also possible and within the scope of the embodiments described herein.

Certain embodiments of the present technology are related to methods for use with an implantable medical device (IMD) having a receiver including first and second differential amplifiers, wherein each the first and second differential amplifiers includes differential inputs and an output, and wherein each of the first and second differential amplifiers is capable of being selectively put in an offset correction phase while enabled. Such a method can include selectively enabling the first and second differential amplifiers such that at any given time at least one of the first and second differential amplifiers is enabled. Such a method can also include selectively putting the first and second differential amplifiers in an offset correction phase such that while the first differential amplifier is enabled and in the offset correction phase the second differential amplifier is enabled without being in the offset correction phase, and such that while the second differential amplifier is enabled and in the offset correction phase the first differential amplifier is enabled without being in the offset correction phase. Additionally, such a method can also include always using at least one of the first and second differential amplifiers to monitor for a predetermined signal (e.g., a wakeup signal) within a frequency range.

In accordance with certain embodiments, in order to conserve power the selectively enabling of the first and second differential amplifiers is performed such that the first and second differential amplifiers are simultaneously enabled for less than 20% (and more preferably, for less than 10%) of a time that only one of the first and second differential amplifiers is enabled.

The receiver including the first and second differential amplifiers can be a first receiver, and the predetermined signal can be a wakeup signal within a first frequency range. In such an embodiment, the method can also include enabling a second receiver in response to the wakeup signal within the first frequency range being detected by at least one of the first and second differential amplifiers of the first receiver, wherein the second receiver consumes more power than the first receiver while the second receiver is enabled. The method can further include using the second receiver to receive one or more implant-to-implant (i2i) communication signals within a second frequency range that is higher than the first frequency range while the second receiver is enabled.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views:

FIG. 2C is an exemplary timing diagram associated with enable and offset correction signals provided to each of the differential amplifiers of the receiver whose details are introduced with reference to FIG. 2B, according to certain embodiments of the present technology.

DETAILED DESCRIPTION

As mentioned above, where conductive communication is utilized for i2i communication, a received signal is likely to have a low amplitude, e.g., be under 1 mV in amplitude. Accordingly, in such a system the use of a traditional differential amplifier is not useful as the input offset voltage of the integrated amplifier will typically be greater than 1 mV, e.g., likely 10 mV or more with additional variation over time and temperature. Additionally, a traditional differential amplifier is very susceptible to input offset voltage drift, which is undesirable when attempting to detect low amplitude i2i signals.

Instead of using a differential amplifier, a single ended amplifier may instead be used. However, this would mandate the use of a very quiet power supply for the receiver since a single ended topology has very poor power supply rejection ratio. This type of receiver is very sensitive to power supply noise and may falsely trigger due to power supply and other noise sources.

Instead of using a traditional differential amplifier, or a single ended amplifier, an auto-zeroed differential amplifier could be used remove the input offset voltage issue. However, during the auto-zero time (also referred to as the auto-zero phase) the amplifier would be "blind" to i2i messages, meaning that the auto-zeroed differential amplifier may not detect an i2i message while being auto-zeroed. This may not be acceptable in a dual chamber pacemaker system, since this may result in synchrony between two implantable medical devices being lost, which may result in a dangerous situation.

Certain embodiments of the present technology relate to a redundant parallel fully differential auto-zeroed system which combines the low input offset voltage, and thus, the high sensitivity of a low offset differential system but without the time period where the system is "blind" due to the auto-zero function. More generally, certain embodiments of the present invention utilize a pair of differential input amplifiers that are selectively enabled in and selectively offset corrected in antiphase in a manner that consumes only slightly more current than would be consumed by one differential input amplifier.

Before providing addition details of the specific embodiments of the present technology mentioned above, an exemplary system in which embodiments of the present technology can be used will first be described with reference to FIGS. 1-5. More specifically, FIGS. 1-5 will be used to describe an exemplary cardiac pacing system, wherein pacing and sensing operations can be performed by multiple medical devices, which may include one or more leadless cardiac pacemakers, an ICD, such as a subcutaneous-ICD, and/or a programmer reliably and safely coordinate pacing and/or sensing operations.

Figure 1:
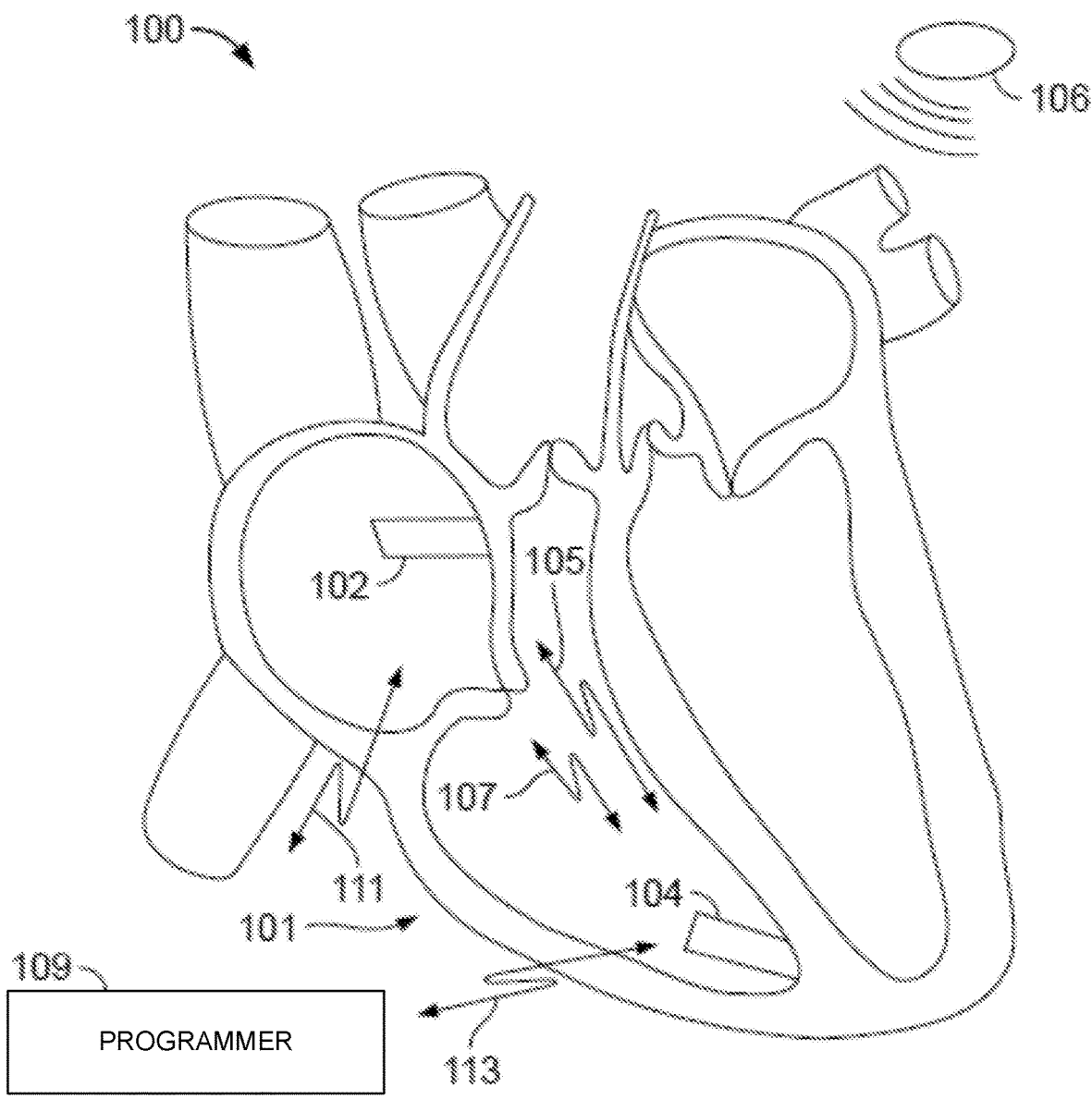
FIG. 1 illustrates a system formed in accordance with certain embodiments herein as implanted in a heart.

FIG. 1 illustrates a system 100 that is configured to be implanted in a heart 101. The system 100 includes two or more leadless pacemakers (LPs) 102 and 104 located in different chambers of the heart. LP 102 is located in a right atrium, while LP 104 is located in a right ventricle. LPs 102 and 104 communicate with one another to inform one another of various local physiologic activities, such as local intrinsic events, local paced events and the like. LPs 102 and 104 may be constructed in a similar manner, but operate differently based upon which chamber LP 102 or 104 is located.

In certain embodiments, LPs 102 and 104 communicate with one another, and/or with an ICD 106, by conductive communication through the same electrodes that are used for sensing and/or delivery of pacing therapy. The LPs 102 and 104 may also be able to use conductive communications to communicate with an external device, e.g., a programmer 109, having electrodes placed on the skin of a patient within with the LPs 102 and 104 are implanted. While not shown (and not preferred, since it would increase the size of the LPs 102 and 104), the LPs 102 and 104 can potentially include an antenna and/or telemetry coil that would enable them to communicate with one another, the ICD 106 and/or an external device using RF or inductive communication.

In some embodiments, one or more leadless cardiac pacemakers 102 and 104 can be co-implanted with the implantable cardioverter-defibrillator (ICD) 106. Each leadless cardiac pacemaker 102, 104 uses two or more electrodes located within, on, or within a few centimeters of the housing of the pacemaker, for pacing and sensing at the cardiac chamber, for bidirectional communication with one another, with the programmer 109, and the ICD 106.

In accordance with certain embodiments, devices and methods are provided for coordinating operation between leadless pacemakers (LPs) located in different chambers of the heart. The devices and methods enable a local LP to receive communications from a remote LP through conductive communication.

While the methods, devices and systems described herein include examples primarily in the context of LPs, it is understood that the methods, devices and systems described herein may be utilized with various other external and implanted devices. By way of example, the methods, devices and systems may coordinate operation between various implantable medical devices (IMDs) implanted in a human, not just LPs. Certain embodiments enable a first IMD to receive communications from at least a second IMD through conductive communication over at least a first channel. It should also be understood that the embodiments described herein can be used for communication between multiple IMDs, and are not limited to communication between just a first and second IMD. The methods, devices and systems may also be used for communication between two or more IMDs implanted within the same chamber that may be the same type of IMD or may be different types of IMDs. The methods, devices and systems may also be used for communication between two or more IMDs in a system including at least one IMD implanted but not within a heart chamber, e.g., epicardially, transmurally, intravascularly (e.g., coronary sinus), subcutaneously (e.g., S-ICD), etc.

Figure 2A:
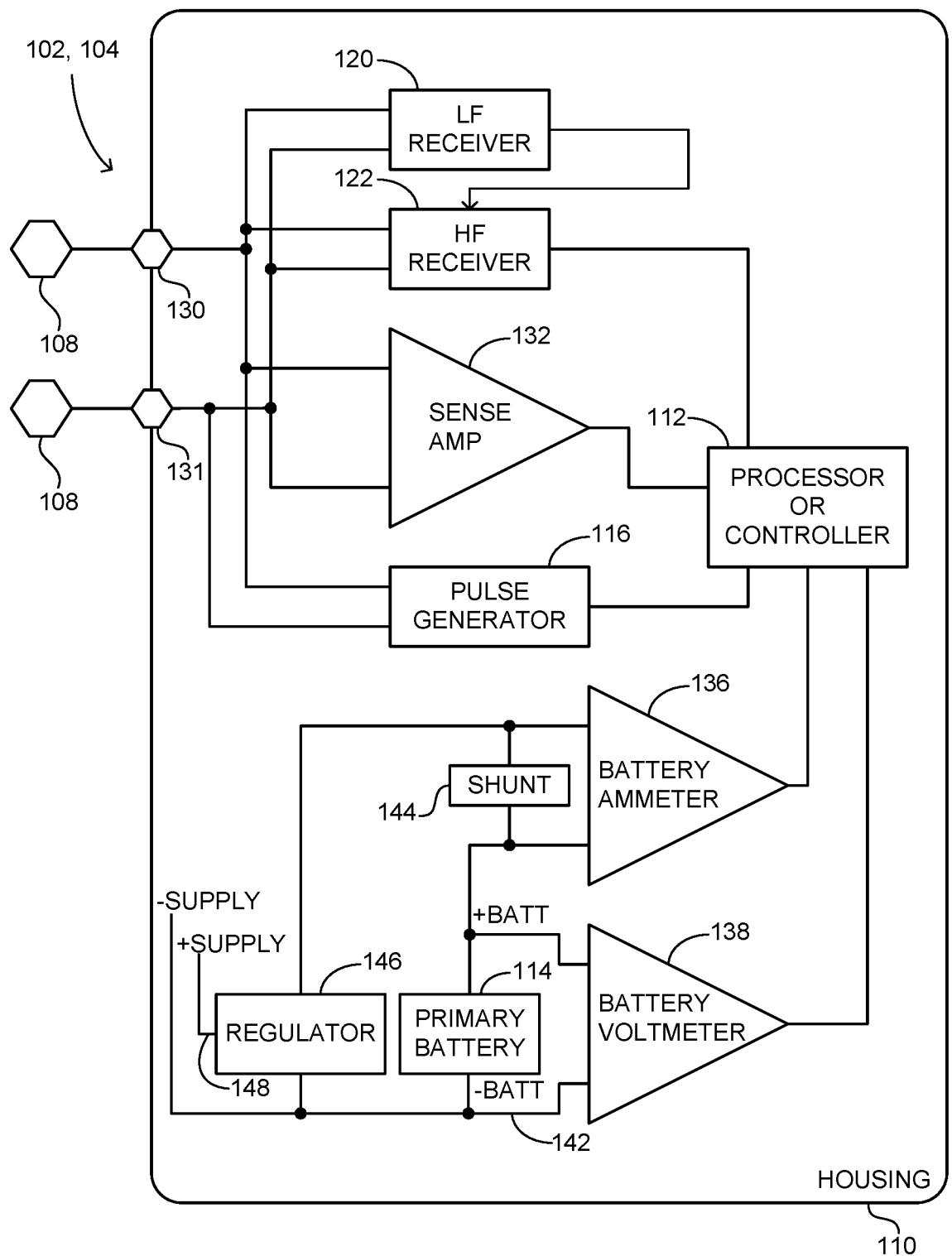
FIG. 2A is a block diagram of a single LP in accordance with certain embodiments herein.

Referring to FIG. 2A, a block diagram shows an embodiment for portions of the electronics within LP 102, 104 configured to provide conductive communication through the sensing/pacing electrode. One or more of LPs 102 and 104 include at least two leadless electrodes 108 configured for delivering cardiac pacing pulses, sensing evoked and/or natural cardiac electrical signals, and uni-directional or bi-directional communication.

LP 102, 104 includes first and second receivers 120 and 122 that collectively define separate first and second communication channels 105 and 107 (FIG. 1), (among other things) between LPs 102 and 104. Although first and second receivers 120 and 122 are depicted, in other embodiments, LP 102, 104 may only include first receiver 120, or may include additional receivers other than first and second receivers 120 and 122. As will be described in additional detail below, the pulse generator 116 can function as a transmitter that transmits i2i communication signals using the electrodes 108. In certain embodiments, LPs 102 and 104 may communicate over more than just first and second communication channels 105 and 107. In certain embodiments, LPs 102 and 104 may communicate over one common communication channel 105. More specifically, LPs 102 and 104 can communicate conductively over a common physical channel via the same electrodes 108 that are also used to deliver pacing pulses. Usage of the electrodes 108 for communication enables the one or more leadless cardiac pacemakers 102 and 104 to perform antenna-less and telemetry coil-less communication.

The receivers 120 and 122 can also be referred to, respectively, as a low frequency (LF) receiver 120 and a high frequency (HF) receiver 122, because the receiver 120 is configured to monitor for one or more signals within a relatively low frequency range (e.g., below 100 kHz) and the receiver 122 is configured to monitor for one or more signals within a relatively high frequency range (e.g., above 100 kHz). In certain embodiments, the receiver 120 (and more specifically, at least a portion thereof) is always enabled and monitoring for a wakeup notice, which can simply be a wakeup pulse, within a specific low frequency range (e.g., between 1 kHz and 100 kHz); and the receiver 122 is selectively enabled by the receiver 120. The receiver 120 is configured to consume less power than the receiver 122 when both the first and second receivers are enabled. Accordingly, the receiver 120 can also be referred to as a low power receiver 120, and the receiver 122 can also be referred to as a high power receiver 122. Additional details of the receiver 120, according to certain embodiments of the present technology, are described further below with reference to FIGS. 2B and 2C. The low power receiver 120 is incapable of receiving signals within the relatively high frequency range (e.g., above 100 kHz), but consumes significantly less power than the high power receiver 122. This way the low power receiver 120 is capable of always monitoring for a wakeup notice without significantly depleting the battery (e.g., 114) of the LP. In accordance with certain embodiments, the high power receiver 122 is selectively enabled by the low power receiver 120, in response to the low power receiver 120 receiving a wakeup notice, so that the high power receiver 122 can receive the higher frequency signals, and thereby handle higher data throughput needed for effective i2i communications without unnecessarily and rapidly depleting the battery of the LP (which the high power receiver 122 may do if it were always enabled).

In accordance with certain embodiments, when one of the LPs 102 and 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

The implant event messages may be formatted in various manners. As one example, each event message may include a leading trigger pulse (also referred to as an LP wakeup notice, wakeup pulse or wakeup signal) followed by an event marker. The notice trigger pulse (also referred to as the wakeup notice, wakeup pulse or wakeup signal) is transmitted over a first channel (e.g., with a pulse duration of approximately 10 μs to approximately 1 ms and/or within a fundamental frequency range of approximately 1 kHz to approximately 100 kHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or other IMD) that receives any implant to implant (i2i) communication from another LP (or other IMD) or from an external device may transmit a receive acknowledgement indicating that the receiving LP/IMD received the i2i communication, etc.

The event messages enable the LPs 102, 104 to deliver synchronized therapy and additional supportive features (e.g., measurements, etc.). To maintain synchronous therapy, each of the LPs 102 and 104 is made aware (through the event messages) when an event occurs in the chamber containing the other LP 102, 104. Some embodiments described herein provide efficient and reliable processes to maintain synchronization between LPs 102 and 104 without maintaining continuous communication between LPs 102 and 104. In accordance with certain embodiments herein, low power event messages/signaling may be maintained between LPs 102 and 104 synchronously or asynchronously.

For synchronous event signaling, LPs 102 and 104 maintain synchronization and regularly communicate at a specific interval. Synchronous event signaling allows the transmitter and receivers in each LP 102,104 to use limited (or minimal) power as each LP 102, 104 is only powered for a small fraction of the time in connection with transmission and reception. For example, LP 102, 104 may transmit/receive (Tx/Rx) communications in time slots having duration of 10-20 μs, where the Tx/Rx time slots occur periodically (e.g., every 10-20 ms).

LPs 102 and 104 may lose synchronization, even in a synchronous event signaling scheme. As explained herein, features may be included in LPs 102 and 104 to maintain device synchronization, and when synchronization is lost, LPs 102 and 104 undergo operations to recover synchronization. Also, synchronous event messages/signaling may introduce a delay between transmissions which causes a reaction lag at the receiving LP 102, 104. Accordingly, features may be implemented to account for the reaction lag.

During asynchronous event signaling, LPs 102 and 104 do not maintain communication synchronization. During asynchronous event signaling, one or more of receivers 120 and 122 of LPs 102 and 104 may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel attenuation may be estimated to have a gain of $\frac{1}{500}$ to $\frac{1}{10000}$. A gain factor may be $\frac{1}{1000}$th. Transmit current is a design factor in addition to receiver current. As an example, the system may allocate one-half of the implant communication current budget to the transmitter (e.g., 0.5 μA for each transmitter). When LP 102, 104 maintains a transmitter in a continuous on-state and the electrode load is 500 ohms, a transmitted voltage may be 2.5V. When an event signal is transmitted at 2.5V, the event signal is attenuated as it propagates and would appear at LP 102, 104 receiver as an amplitude of approximately 0.25 mV.

To overcome the foregoing receive power limit, a pulsed transmission scheme may be utilized in which communication transmissions occur correlated with an event. By way of example, the pulsed transmission scheme may be simplified such that each transmission constitutes a single pulse of a select amplitude and width.

In accordance with certain embodiments herein, LPs 102 and 104 may utilize multi-stage receivers that implement a staged receiver wakeup scheme in order to improve reliability yet remain power efficient. Each of LPs 102 and 104 may include first and second receivers 120 and 122 that operate with different first and second activation protocols and different first and second receive channels. For example, first receiver 120 may be assigned a first activation protocol that is "always on" (also referred to as always awake) and that listens over a first receive channel that has a lower fundamental frequency range/pulse duration (e.g., 1 kHz to 100 kHz/10 µs to approximately 1 ms) as compared to the fundamental frequency range (e.g., greater than 100 kHz/less than 10 µs per pulse) assigned to the second receive channel.

In accordance with certain embodiments, the first receiver 120 may maintain the first channel active (awake) at all times (including when the second channel is inactive (asleep)) in order to listen for messages from a remote LP. The second receiver 122 may be assigned a second activation protocol that is a triggered protocol, in which the second receiver 122 becomes active (awake) in response to detection of trigger events over the first receive channel (e.g., when the incoming signal corresponds to the LP wakeup notice, activating the second channel at the local LP). The terms active, awake and enabled are used interchangeably herein.

Still referring to FIG. 2A, each LP 102, 104 is shown as including a processor or controller 112 and a pulse generator 116. The processor or controller 112 can include, e.g., a microprocessor (or equivalent control circuitry), RAM and/or ROM memory, logic and timing circuitry, state machine circuitry, and I/O circuitry, but is not limited thereto. The processor or controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The processor or controller 112 can further include other dedicated circuitry and/or firmware/software components that assist in monitoring various conditions of the patient's heart and managing pacing therapies. The processor or controller 112 and the pulse generator 116 may be configured to transmit event messages, via the electrodes 108, in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with certain embodiments herein, programmer 109 may communicate over a programmer-to-LP channel, with LP 102, 104 utilizing the same communication scheme. The external programmer may listen to the event message transmitted between LP 102, 104 and synchronize programmer to implant communication such that programmer 109 does not transmit communication signals 113 until after an implant to implant messaging sequence is completed.

In accordance with certain embodiments, LP 102, 104 may combine transmit operations with therapy. The transmit event marker may be configured to have similar characteristics in amplitude and pulse-width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 µA. The same LP 102, 104 may implement an event message utilizing event signaling parameters for amplitude, pulse-width, pulse rate, etc. that correspond to a current draw of approximately 0.5 µA for transmit.

LP 102, 104 may combine the event message transmissions with pacing pulses. For example, LP 102, 104 may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102 or 104 senses an intrinsic event, it can send a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, LP 102, 104 may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102, 104 increases an extent to which LP 102, 104 uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25V pace pulse would save 1.5 µA of pacing current budget. With lower pulse amplitudes, LP 102, 104 may use larger pulse-widths.

By combining event messages and low power pacing, LP 102, 104 may realize additional longevity. Today longevity standards provide that the longevity to be specified based on a therapy that utilizes 2.5V amplitude, 0.4 ms pulses at 100% pacing. Optionally, a new standard may be established based on pacing pulses that deliver lower amplitude and/or shorter pacing pulses.

While not shown, a communication capacitor can be provided in LP 102, 104. The communication capacitor may be used to transmit event signals having higher voltage for the event message pulses to improve communication, such as when the LPs 102 and 104 experience difficulty sensing event messages. The high voltage event signaling may be used for implants with high signal attenuation or in the case of a retry for an ARQ (automatic repeat request) handshaking scheme.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 2A depicts a single LP 102 (or 104) and shows the LP's functional elements substantially enclosed in a hermetic housing 110. The LP 102 (or 104) has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more leadless cardiac pacemakers 102 and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102, 104 can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to leadless cardiac pacemaker 102, 104 configured for implantation in electrical contact with a cardiac chamber and for performing cardiac rhythm management functions in combination with the implantable ICD 106. The implantable ICD 106 and the one or more leadless cardiac pacemakers 102, 104 configured for leadless intercommunication by information conduction through body tissue and/or wireless transmission between transmitters and receivers in accordance with the discussed herein.

In a further embodiment, a cardiac pacing system 100 comprises at least one leadless cardiac pacemaker 102, 104 configured for implantation in electrical contact with a cardiac chamber and configured to perform cardiac pacing functions in combination with the co-implanted implantable cardioverter-defibrillator (ICD) 106. The leadless cardiac pacemaker or pacemakers 102 comprise at least two leadless electrodes 108 configured for delivering cardiac pacing pulses, sensing evoked and/or natural cardiac electrical signals, and transmitting information to the co-implanted ICD 106.

As shown in the illustrative embodiments, a leadless cardiac pacemaker 102, 104 can comprise two or more leadless electrodes 108 configured for delivering cardiac pacing pulses, sensing evoked and/or natural cardiac electrical signals, and bidirectionally communicating with the co-implanted ICD 106.

LP 102, 104 can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or WI), and for the IPG to utilize the proper set of settings and algorithms (e.g., V-AutoCapture vs ACap-Confirm, sensing sensitivities, etc.).

Also shown in FIG. 2A, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the processor or controller 112 in one leadless cardiac pacemaker 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the processor or controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 3:
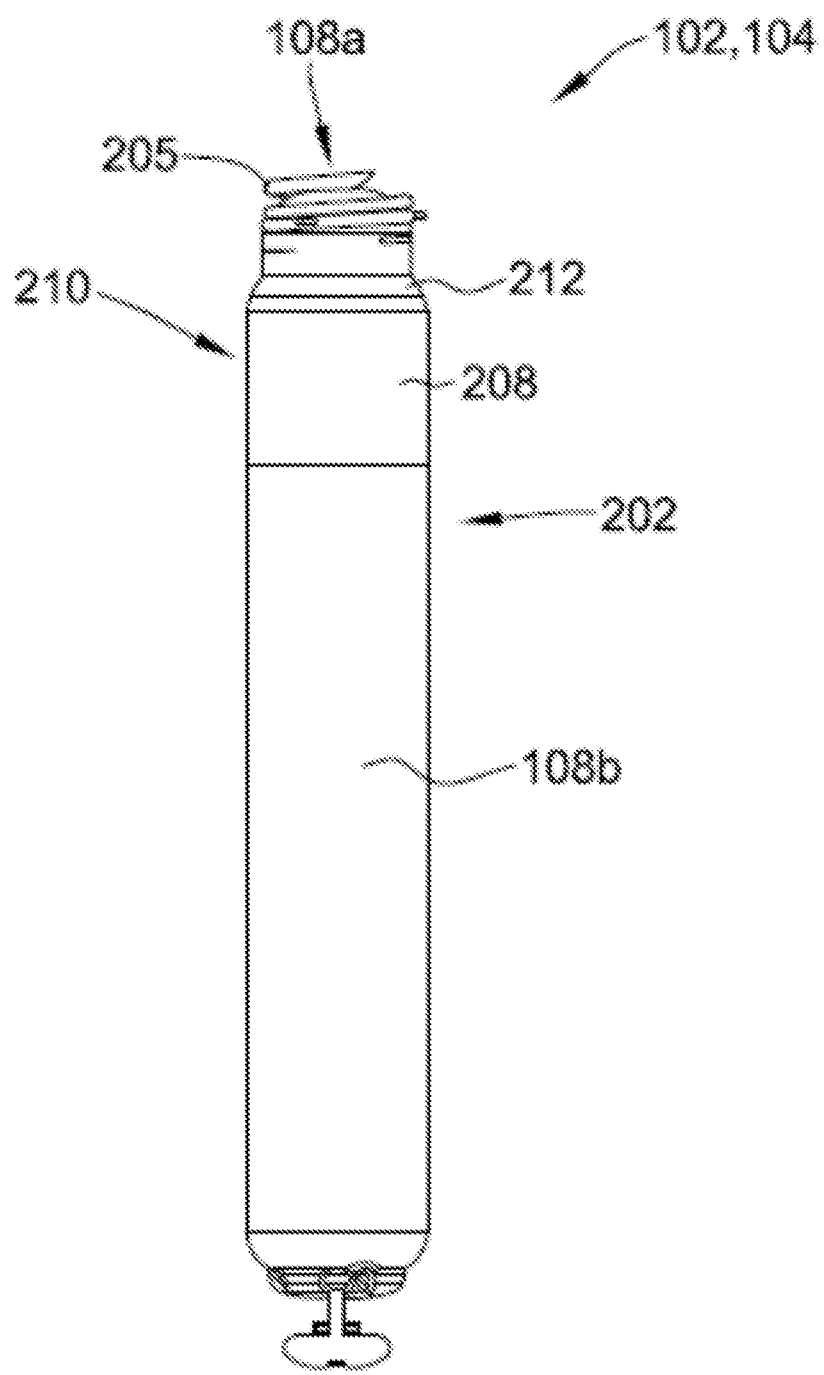
FIG. 3 illustrates an LP in accordance with certain embodiments herein.

FIG. 3 shows an LP 102, 104. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 2A.

The housing can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 3) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant Event Messaging

LPs 102 and 104 can utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In certain embodiments, LP 102 and LP 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 4:
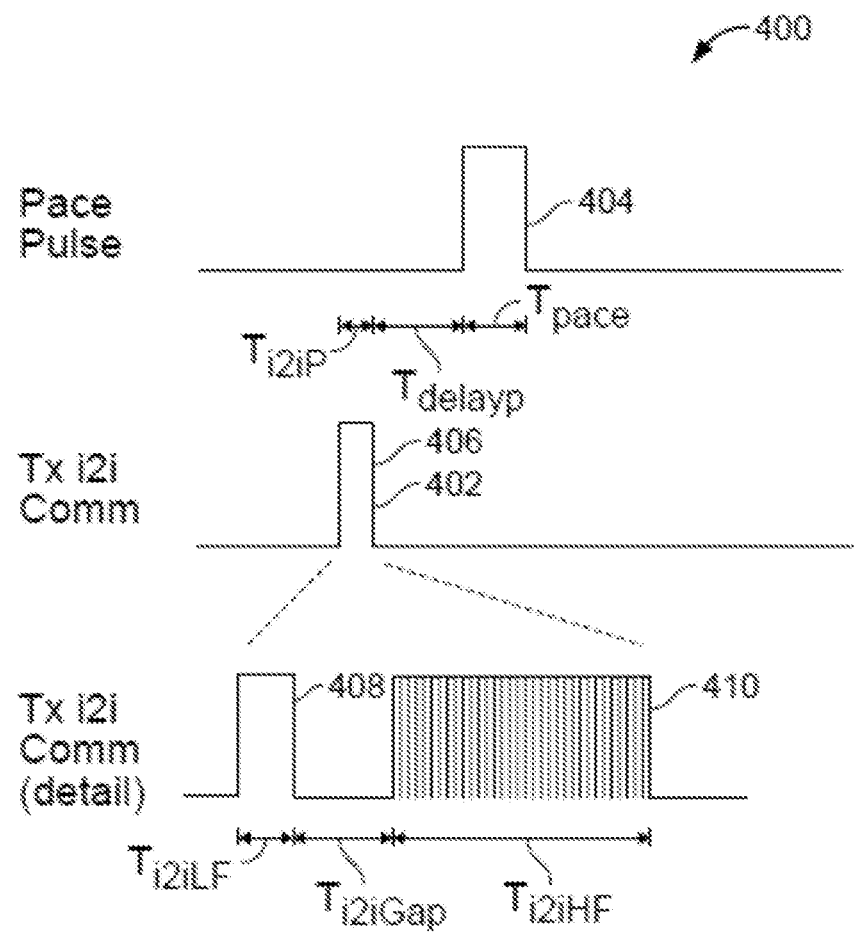
FIG. 4 is a timing diagram demonstrating one embodiment of implant to implant (i2i) communication for a paced event.

FIG. 4 is a timing diagram 400 demonstrating one example of an i2i communication for a paced event. The i2i communication may be transmitted, for example, from LP 102 to LP 104. As shown in FIG. 4, in this embodiment, an i2i transmission 402 is sent prior to delivery of a pace pulse 404 by the transmitting LP (e.g., LP 102). This enables the receiving LP (e.g., LP 104) to prepare for the remote delivery of the pace pulse. The i2i transmission 402 includes an envelope 406 that may include one or more individual pulses. For example, in this embodiment, envelope 406 includes a low frequency pulse 408 followed by a high frequency pulse train 410. Low frequency pulse 408 lasts for a period Ti2iLF, and high frequency pulse train 410 lasts for a period Ti2iHF. The end of low frequency pulse 408 and the beginning of high frequency pulse train 410 are separated by a gap period, Ti2iGap.

As shown in FIG. 4, the i2i transmission 402 lasts for a period Ti2iP, and pace pulse 404 lasts for a period Tpace. The end of i2i transmission 402 and the beginning of pace pulse 404 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means +/−10% of a specified value.

Figure 5:
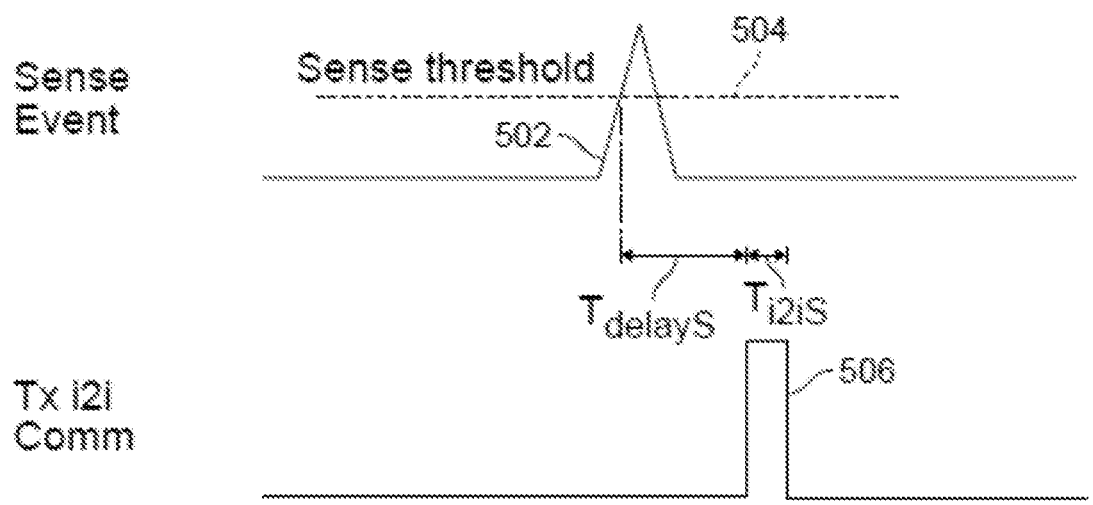
FIG. 5 is a timing diagram demonstrating one embodiment of i2i communication for a sensed event.

FIG. 5 is a timing diagram 500 demonstrating one example of an i2i communication for a sensed event. The i2i communication may be transmitted, for example, from LP 102 to LP 104. As shown in FIG. 5, in this embodiment, the transmitting LP (e.g., LP 102) detects the sensed event when a sensed intrinsic activation 502 crosses a sense threshold 504. A predetermined delay period, TdelayS, after the detection, the transmitting LP transmits an i2i transmission 506 that lasts a predetermined period Ti2iS. The delay period may be, for example, between approximately 0.0 and 10.0 milliseconds (ms), particularly between approximately 0.1 ms and 2.0 ms, and more particularly approximately 1.0 ms.

As with i2i transmission 402, i2i transmission 506 may include an envelope that may include one or more individual pulses. For example, similar to envelope 406, the envelope of i2i transmission 506 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication can include event messages transmitted from the sensing/pacing electrodes at frequencies outside the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

| "A2V" Markers/Commands (i.e., from aLP to vLP) | | |
|---|---|---|
| Marker | Description | Result in vLP |
| AS | Notification of a sensed event in atrium (if not in PVAB or PVARP) | Initiate AV interval (if not in PVAB or PVARP) |
| AP | Notification of a paced event in atrium | Initiate PAVB Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a WI mode as the vLP does not depend on i2i communication to perform ventricular pace/sense activities. Once i2i communication is restored, the system 100 can automatically resume dual-chamber functionalities.

Always on Receiver with Offset Correction

As noted above, in the discussion of FIG. 2A, each of the LPs 102, 104 includes first and second receivers 120 and 122, which can also be referred to respectively as LF and HF receivers 120 and 122, or low power and high power receivers 120 and 122. In accordance with certain embodiments, the LF receiver 120 is configured to monitor for a wakeup signal within a relatively low frequency range (e.g., below 100 kHz), and the receiver 122 (when enabled) is configured to monitor for event message signals within a relatively high frequency range (e.g., above 100 kHz). In certain embodiments, the receiver 120 (and more specifically, at least a portion thereof) is always enabled and monitoring for a wakeup notice, which can simply be a wakeup pulse, within a specific low frequency range (e.g., between 1 kHz and 100 kHz); and the receiver 122 is selectively enabled by the receiver 120. The receiver 120 is configured to consume less power than the receiver 122 when both the first and second receivers are enabled. For example, the receiver 122 may consume about 50 µA when enabled, and the receiver 120 may consume on average only about 0.3 µA.

In accordance with certain embodiments, the wakeup signal that the receiver 120 is configured to monitor for and detect for has a low amplitude that may be under 1 mV. Accordingly, it would not be useful to implement the receiver 120 using a traditional differential amplifier because the input offset voltage of a traditional differential amplifier will typically be greater than 1 mV (e.g., likely 10 mV or more with additional variation over time and temperature). Additionally, a traditional differential amplifier is very susceptible to input offset voltage drift, which is undesirable when attempting to detect low amplitude signals of 1 mV or less.

Instead of using a traditional differential amplifier to implement the receiver 120, a single ended amplifier may be used. However, this would undesirably mandate the use of a very quite power supply for the receiver 120 since a single ended topology has very poor power supply rejection ratio. It would be difficult to implement such a quiet power supply within an IMD, such as the LP 102, 104.

Another option would be to implement the receiver 120 using an auto-zeroed differential amplifier, which could remove the input offset voltage issue. However, during its auto-zero phase, the auto-zeroed differential amplifier would not be able to detect a signal sent from another LP, and thus, would be blind to a wakeup signal sent from another LP (or from an external programmer 109). This would not be acceptable in a dual chamber pacemaker system because synchrony between the two LPs 102 and 104 could be lost, resulting in a potentially dangerous situation.

In accordance with certain embodiments of the present technology, which initially will be described with reference to FIG. 2B, two auto-zeroed differential amplifiers (or more generally, differential amplifiers capable of being selectively offset corrected) are used in parallel and antiphase to implement the receiver 120. Such embodiments provide for low input offset voltage, and thus, the high sensitivity of low offset differential system, in a manner that avoids the receiver 120 being blind to wakeup signals during an auto-zero phase (or more generally, an offset correction phase), as will be better understood from the below discussion of FIG. 2B.

Figure 2B:
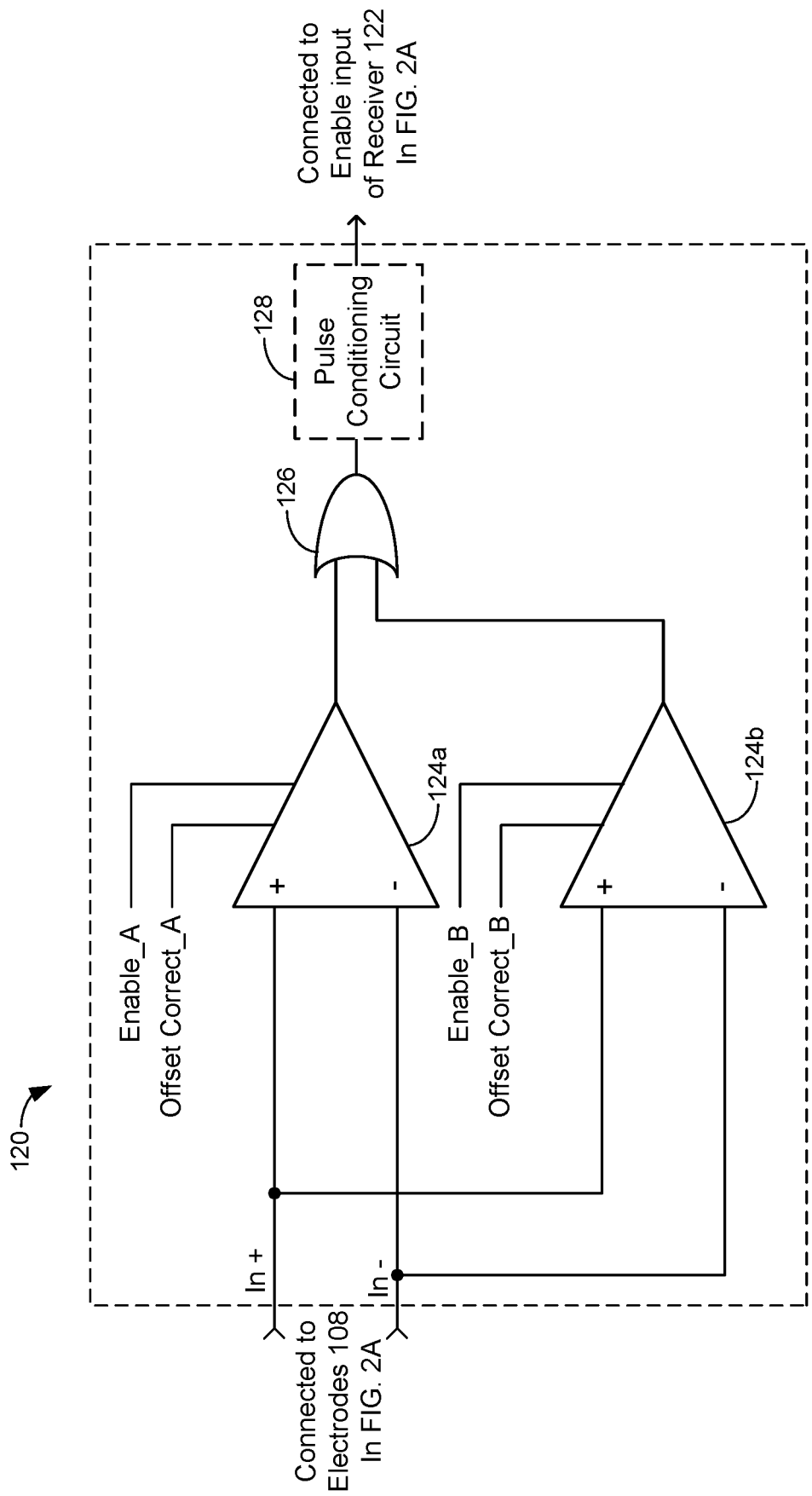
FIG. 2B provides additional details of one of the receivers of the LP introduced with reference to FIG. 2A, according to certain embodiments of the present technology.

Referring to FIG. 2B, the receiver 120 is shown as including two differential amplifiers 124a and 124b, each of which includes differential inputs and an output. The differential amplifiers 124a and 124b can be referred to collectively as the differential amplifiers 124, or individually as a differential amplifier 124. Each of the differential amplifiers 124 includes a respective enable terminal that allows each of the differential amplifiers 124 to be selectively enabled. Each of the differential amplifiers 124, while enabled, drains current (e.g., ~300 nA) and thereby power from the battery. Conversely, each of the differential amplifiers 124, while not enabled, drains substantially no current (i.e., less than 10 nA) and thus substantially no power (i.e., less than 20 nA) from the battery 114. Each of the differential amplifiers 124 also includes a respective offset correction terminal that enables each of the differential amplifiers 124 (while enabled) to be selectively offset corrected. Depending upon implementation, each of the differential amplifiers 124 can be configured to be enabled in response to the signal at its enable terminal being HIGH (or alternatively, in response to the signal at its enable terminal being LOW). Depending upon implementation, each of the differential amplifiers 124 can be configured to be offset corrected (while enabled) in response to the signal at its offset correction terminal being HIGH (or alternatively, in response to the signal at its offset correction terminal being LOW). When a differential amplifier 124 is not enabled, it can also be said that the differential amplifier 124 is disabled. When a differential amplifier 124 is enabled and not in its offset correction phase (i.e., not being offset corrected), it can be said that the differential amplifier 124 is in its normal sensing and amplifying phase.

In accordance with certain embodiments, each of the differential amplifiers 124 is implemented as an auto-zeroed differential amplifier, in which case the offset correction phase is more specifically an auto-zero phase during which the differential amplifier 124 is auto-zeroed to remove an input offset voltage. In accordance with alternative embodiments, each of the differential amplifiers 124 is implemented as a chopper-stabilized differential amplifier, in which case the offset correction phase is more specifically a chopper-stabilization phase. Other variations are possible, and within the scope of embodiments of the present technology described herein.

In accordance with certain embodiments, each of the differential amplifiers 124, while enabled, is configured to monitor for a wakeup signal. As explained above with reference to FIG. 4, the wakeup signal can be low amplitude (e.g., 1 mV) and low frequency pulse 408 (that is followed by a low amplitude and high frequency pulse train 410). For a more specific example, the wakeup signal can be a 1 mV pulse having a pulse-width of 20 μs, in which case each of the differential amplifiers can be specifically tuned to monitor for and detect a 1 mV wakeup pulse having a 20 μs pulse-width.

The signal that is output from each of the differential amplifiers 124 can be referred to as an amplified difference signal. Depending upon implementation, each of the differential amplifiers 124 can be configured to nominally output a LOW amplified difference signal (when the wakeup pulse is not detected) and output a HIGH amplified difference signal in response to the wakeup pulse being detected. Alternatively, although unlikely, each of the differential amplifiers 124 can be configured nominally output a HIGH amplified difference signal (when the wakeup pulse is not detected) and output a LOW amplified difference signal in response to the wakeup pulse being detected. For the remainder of this discussion, it will be assumed that each of the differential amplifiers 124 is configured nominally output a LOW amplified difference signal (when the wakeup pulse is not detected) and output a HIGH amplified difference signal in response to the wakeup pulse being detected.

During its offset correction phase (e.g., auto-zero phase, or chopper stabilization phase), a differential amplifier 124 is unable to detect the signal (e.g., the wakeup pulse) that the differential amplifier 124 is configured to monitor for, and thus, the amplified difference signal produced at the output of the differential amplifier 124 will not be indicative of whether or not the predetermined signal (e.g., the wakeup pulse) is detected by the differential amplifier 124. For example, while a differential amplifier 124 is in its offset correction phase, the amplified difference signal output by the differential amplifier 124 may hover about halfway between a LOW and HIGH output level. Accordingly, in accordance with certain embodiments, the amplified difference signal output by a differential amplifier 124 is ignored when the differential amplifier 124 is in its offset correction phase (e.g., its auto-zero phase, or its chopper stabilization phase). In other words, in accordance with certain embodiments, the output of a differential amplifier 124 is ignored when the differential amplifier 124 is in its offset correction phase.

Still referring to FIG. 2B, the outputs of the differential amplifiers 124a and 124b are shown as being provided to respective inputs of an OR gate circuit 126, which is used to combine the outputs of the differential amplifiers 124a and 124b. More specifically, the output of the OR gate circuit 126 will go HIGH in response to at least one of the inputs to the OR gate circuit 126 going HIGH. One of the inputs to the OR gate circuit 126 will be HIGH when one of the differential amplifiers 124a and 124b detects the wakeup signal (e.g., the wakeup pulse) that the differential amplifiers 124a and 124b are each monitoring for. Accordingly, the output of the OR gate 126 will go HIGH, and cause the receiver 122 to be enabled, in response to one of the differential amplifiers 124a and 124b detecting the wakeup signal they are monitoring for. The output of the OR gate circuit 126 can be provided directly to the enable terminal of the receiver 122. Alternatively, an optional pulse conditioning circuit 128 is located between the output of the OR gate circuit 126 and the enable terminal of the receiver 122. The pulse conditioning circuit 128 can, for example, stretch the pulse output by the OR gate circuit 126 to a desired pulse-width. Alternatively, the pulse conditioning circuit 128 can be configured to output a pulse of a specific amplitude and pulse-width in response to the input of the pulse conditioning circuit 128 going from LOW to HIGH and remaining HIGH for at least a predetermined period of time. Other variations are also possible, and within the scope of the embodiments of the present technology. More generally, other ways of combining the outputs of the differential amplifiers 124a and 124b into one signal, besides using the OR gate circuit 126, are possible and are within the scope of the embodiments of the present technology described herein.

In accordance with certain embodiments of the present technology, at any given time at least one of the differential amplifiers 124a and 124b of the receiver 120 is enabled without being in the offset correction phase (e.g., the auto-zero phase, or the chopper stabilization phase). This beneficially enables at least one of the differential amplifiers 124a and 124b to always be monitoring for the wakeup signal within its expected low frequency range. More specifically, in accordance with certain embodiments of the present technology, each of the differential amplifiers 124a and 124b is periodically offset corrected, during which time the other one of the differential amplifiers 124a and 124b is enabled and not being offset corrected and is thereby monitoring for the wakeup signal. Accordingly, it should be appreciated that there will be times that both of the differential amplifiers 124a and 124b are simultaneously enabled, and thus, times that both of the differential amplifiers 124a and 124b are draining current and thereby power from the battery 114.

In order to substantially minimize the power that the receiver 120 drains from the battery 114, the amount of time that both differential amplifiers 124a and 124b are both enabled should be kept low and preferably minimized. In accordance with certain embodiments, for at least a majority of time that both differential amplifiers 124a and 124b are enabled, one of the differential amplifiers 124a and 124b is being offset corrected. For example, assume that it takes 3 ms for an offset correction phase to be completed. If the amount of time that both of the differential amplifiers 124a and 124b are both enabled is 4 ms per cycle period (e.g., per 100 ms), then for at least a majority of time that both differential amplifiers 124a and 124b are enabled, one of the differential amplifiers 124a and 124b is being offset corrected. Preferably, the amount of time that both differential amplifiers 124a and 124b are enabled without either of them being offset corrected is substantially minimized, in order to substantially minimize the power drawn by the receiver 120 that includes the differential amplifiers 124a and 124b. In accordance with certain embodiments, the differential amplifiers 124a and 124b are simultaneously enabled for less than 20% (and preferably, less than 10%) of a time that only the differential amplifiers 124a and 124b is enabled.

For an example, assume that during each 64 ms cycle period, each of the differential amplifiers 124a and 124b is selectively enabled for 36 ms. Also assume that only one of the differential amplifiers 124a and 124b is enabled for 28 ms during each 64 ms cycle period, and that both of the differential amplifiers are enabled for 4 ms during each 64 ms cycle period. In this example, during each 64 ms cycle period, the differential amplifiers 124a and 124b are simultaneously enabled for ~14% of the time that that only one of the differential amplifiers 124a and 124b is enabled (i.e., 4 ms/28 ms=0.14286). This would satisfy the requirement that the differential amplifiers 124a and 124b are simultaneously enabled for less than 20% of a time that only one of the differential amplifiers 124a and 124b is enabled.

FIG. 2C is an exemplary timing diagram for Enable_A and Offset_correct_A signals that are provided respectively to the enable terminal and the offset correct terminal of the differential amplifier 124a, and the Enable_B and Offset_correct_B signals that are provided respectively to the enable terminal and the offset correct terminal of the differential amplifier 124b. In this example, during each 100 ms cycle period each of the differential amplifiers 124a and 124b is selectively enabled for 54 ms, only one of the differential amplifiers 124a and 124b is enabled for 46 ms during each 100 ms cycle period, and both of the differential amplifiers are enabled for 4 ms during each 100 ms cycle period. Accordingly, in this example, during each 100 ms cycle period, the differential amplifiers 124a and 124b are simultaneously enabled for ~8.7% of the time that that only one of the differential amplifiers 124a and 124b is enabled (i.e., 4 ms/46 ms=0.08696). This would satisfy the requirement that the differential amplifiers 124a and 124b are simultaneously enabled for less than 20% of a time that only one of the differential amplifiers 124a and 124b is enabled. Indeed in this example, the differential amplifiers 124a and 124b are simultaneously enabled for less than 10% of the time that only one of the differential amplifiers 124a and 124b is enabled. Preferably, the amount of time that both differential amplifiers 124a and 124b are simultaneously enabled is substantially minimized, and will depend at least in part upon how quickly the differential amplifiers 124 are capable of being offset corrected, and the length of the cycle periods. The processor or controller 112 (in FIG. 2A) can be used to generate the signals shown in FIG. 2C. Additionally, or alternatively, clock circuitry (not specifically shown) can be used to produce the signals shown in FIG. 2C, potentially under the control of the processor or controller 112. Other variations are also possible and within the scope of the embodiments described herein.

In accordance with certain embodiments of the present technology, after the receiver 122 is enabled (by the receiver 120, in response to the receiver 120 detecting the wakeup signal), the receiver 122 can receive one or more i2i communication signals within a frequency range that is higher than the frequency range within which the receiver 120 received the wakeup signal. More generally, the receiver 122 once enable can receive signals within a higher frequency range than the receiver 120 is capable of receiving signals. The i2i communication signal(s) received by the receiver 122 can be provided to the processor or controller 112 and used by the processor or controller 122 to start an interval timer (e.g., an AV interval timer) that is used to trigger delivery of a pacing pulse via the electrodes 108. Such a pacing pulse can be produced by the pulse generator 116. Other variations are also possible and within the scope of the embodiments described herein.

Figure 6:
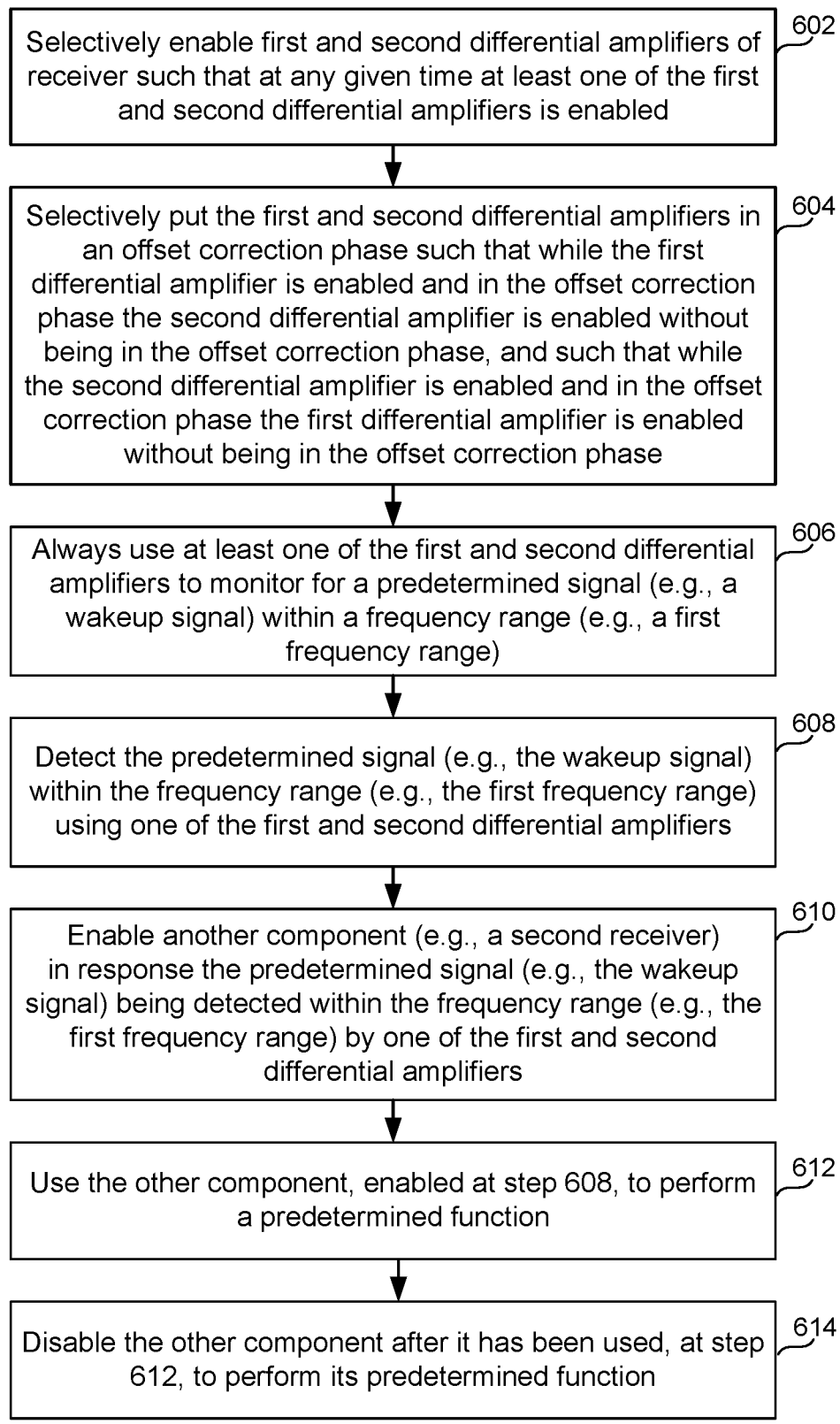
FIG. 6 is high level flow diagram that are used to summarize methods according to certain embodiments of the present technology.

FIG. 6 is high level flow diagram that are used to summarize methods according to certain embodiments of the present technology. Such methods can be used with an implantable medical device (IMD) having a receiver including first and second differential amplifiers, wherein each the first and second differential amplifiers includes differential inputs and an output, and wherein each of the first and second differential amplifiers is capable of being selectively put in an offset correction phase while enabled. An example of an IMD with which such methods can be performed is the LP 102, 104 described above with reference to FIGS. 2A-2C. More specifically, FIG. 2B, described above, provides exemplary details of a receiver 120 including two differential amplifiers 124a and 124b that include differential inputs and an output, and that are capable of being selectively put in an offset correction phase while enabled.

Referring to FIG. 6, step 602 involves selectively enabling the first and second differential amplifiers such that at any given time at least one of the first and second differential amplifiers is enabled. In accordance with certain embodiments, examples of which were discussed above, step 602 is performed such that the first and second differential amplifiers are simultaneously enabled for less than 20% of a time that only one of the first and second differential amplifiers is enabled.

Still referring to FIG. 6, step 604 involves selectively putting the first and second differential amplifiers in an offset correction phase such that while the first differential amplifier is enabled and in the offset correction phase the second differential amplifier is enabled without being in the offset correction phase, and such that while the second differential amplifier is enabled and in the offset correction phase the first differential amplifier is enabled without being in the offset correction phase. An exemplary timing diagram that can be used to perform step 604, as well as step 602, is shown in and described above with reference to FIG. 2C. In accordance with certain embodiments, each of the first and second differential amplifiers is an auto-zero differential amplifier, in which case the offset correction phase is an auto-zero phase. In accordance with other embodiments, each of the first and second differential amplifiers is a chopper-stabilized differential amplifier, in which case the offset correction phase is a chopper-stabilization phase.

Step 606 involves always using at least one of the first and second differential amplifiers to monitor for a predetermined signal within a frequency range. In accordance with certain embodiments, the predetermined signal is a wakeup signal, and more specifically, can be a wakeup pulse. In accordance with certain embodiments, the frequency range within which the wakeup signal is monitor for is within a low frequency range, which can be, e.g., between 1 kHz and 100 kHz, but is not limited thereto.

Step 608 involves detecting the predetermined signal (e.g., the wakeup signal) within the frequency range (e.g., the first frequency range) using one of the first and second differential amplifiers of the receiver.

Step 610 involves enabling another component of the IMD in response to the predetermined signal being detected within the frequency range by one of the first and second differential amplifiers. In accordance with certain embodiments, the receiver that includes the first and second differential amplifiers can be a first receiver (e.g., the receiver 120 in FIGS. 2A and 2B). Further, as noted above, the predetermined signal that the differential amplifiers are configured to monitor for and detect can be a wakeup signal within a first frequency range. In such embodiments, step 610 can can involve enabling a second receiver (e.g., the receiver 122 in FIG. 2A) in response to the wakeup signal within the first frequency range being detected by at least one of the first and second differential amplifiers of the first receiver.

Step 612 involves using the other component, which was enabled at step 610, to perform a predetermined function. For example, step 612 can involves using the second receiver (e.g., the receiver 122 in FIG. 2A) to detect one or more implant-to-implant (i2i) communication signals within a second frequency range that is higher than the first frequency range while the second receiver is enabled. As explain above, such a second receiver (e.g., 122) consumes more power than the first receiver (e.g., 120) while the second receiver is enabled.

Step 614 involves disabling the other component (e.g., the receiver 122 in FIG. 2A) after it has been used, at step 612, to perform its predetermined function. Such disabling at step 614 is performed in order to conserver the power of the battery within the IMD that is being used to power the electrical components of the IMD, which components can include, among other components, the first and second differential amplifiers of the first receiver, as well as to power the second receiver while it is enabled.

The steps that are described with reference to FIG. 6 need not be performed in the exact order described, unless the results of one step are being used by another step or are being used to trigger the start of another step. For example, steps 602, 604 and 606, or at least portions thereof, can be performed in parallel. By contrast, since step 610 is performed in response to step 608 being performed, step 610 necessarily occurs after step 608.

While many of the embodiments of the present technology described above have been described as being for use with LP type IMDs, embodiments of the present technology can also be used with other types of IMDs besides an LP. Accordingly, unless specifically limited to use with an LP, the claims should not be limited to use with LP type IMDs.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An implantable medical device (IMD), comprising:
   a first differential amplifier including first differential inputs and a first output at which a first amplified difference signal is output;
   a second differential amplifier including second differential inputs and a second output at which a second amplified difference signal is output;
   first and second electrodes that sense a conductive communication signal transmitted by one of a further IMD or an external programmer;
   the first and the second electrodes electrically coupled to both the first differential inputs of the first differential amplifier and the second differential inputs of the second differential amplifier, such that a same conductive communication signal that is sensed by the first and the second electrodes is provided to both the first differential inputs of the first differential amplifier and the second differential inputs of the second differential amplifier; and
   at least one of a controller, processor and/or clock circuitry that generates one or more signals that are provided to the first and the second differential amplifiers to cause
      the first and the second differential amplifiers to be selectively enabled and auto-zeroed such that at all times at least one of the first and the second differential amplifiers is enabled and not being auto-zeroed, and
      one of the first and the second amplified difference signals to be used, at any given time, to selectively enable a component of the IMD in response to the one of the first and the second differential amplifiers, which is enabled and not being auto-zeroed, detecting a predetermined conductive communication signal within a frequency range.

2. The IMD of claim 1, wherein the IMD comprises a leadless cardiac pacemaker including the first and the second electrodes that are electrically coupled to the differential inputs of each of the first and the second differential amplifiers.

3. The IMD of claim 1, wherein the first and the second differential amplifiers are simultaneously enabled for less than 20% of a time that only one of the first and the second differential amplifiers is enabled.

4. The IMD of claim 3, wherein one of the first and the second differential amplifiers is being auto-zeroed for at least a majority of a time that the first and the second differential amplifiers are simultaneously enabled.

5. The IMD of claim 1, wherein the first and the second differential amplifiers are parts of a first receiver of the IMD, and the component of the IMD that is enabled in response to the predetermined signal being detected comprises a second receiver of the IMD that consumes more power while enabled than the first receiver.

6. The IMD of claim 5, wherein the IMD comprises a cardiac stimulation device and the differential inputs of each of the first and the second differential amplifiers are connected to the first and the second electrodes of the cardiac stimulation device, the first and the second electrodes for use in selectively delivering cardiac stimulation and also for use in sensing conductive communication signals transmitted by at least one of a further IMD or an external programmer.

7. The IMD of claim 6, wherein the predetermined signal that the first and the second differential amplifiers are configured to monitor for comprises a wakeup signal that is sent by a further IMD prior to the further IMD sending an event message.

8. The IMD of claim 7, further comprising an interval timer that is configured to be initiated in response to the IMD receiving the event message from the further IMD, wherein the interval timer is used to trigger delivery of a pacing pulse via the first and the second electrodes.

9. The IMD of claim 7, wherein the IMD is configured to be implanted within or on a wall of a first cardiac chamber and the further IMD from which the wakeup signal and event message is received is configured to be implanted within or on a wall of a second cardiac chamber that differs from the first cardiac chamber.

10. The IMD of claim 1, further comprising a battery, wherein:
each of the first and the second differential amplifiers, while enabled, drains current and thereby power from the battery; and
each of the first and the second differential amplifiers, while not enabled, drains substantially no current and thus substantially no power from the battery.

11. An implantable medical device (IMD), comprising:
a first receiver including first and second differential amplifiers, the first differential amplifier including first differential inputs and a first output at which a first amplified difference signal is output, and the second differential amplifier including second differential inputs and a second output at which a second amplified difference signal is output;
first and second electrodes that sense a conductive communication signal transmitted by one of a further IMD or an external programmer;
the first and the second electrodes electrically coupled to both the first differential inputs of the first differential amplifier and the second differential inputs of the second differential amplifier, such that a same conductive communication signal that is sensed by the first and the second electrodes is provided to both the first differential inputs of the first differential amplifier and the second differential inputs of the second differential amplifier;
a second receiver; and
a battery that powers enabled electrical components of the IMD, including the first and the second differential amplifiers of the first receiver while enabled;
each of the first and the second differential amplifiers, while enabled, configured to monitor for a predetermined signal within a frequency range;
each of the first and the second differential amplifiers, while enabled, draining current and thereby power from the battery;
each of the first and the second differential amplifiers, while not enabled, draining substantially no current and thus substantially no power from the battery; and
each of the first and the second differential amplifiers, while enabled, capable of being selectively put into an auto-zero phase during which time the predetermined signal is not detectable by the differential amplifier;
wherein the first and the second differential amplifiers of the first receiver are selectively enabled and auto-zeroed such that at all times at least one of the first and the second differential amplifiers is enabled and not being auto-zeroed; and
wherein at any given time one of the first and the second amplified difference signals is used to selectively enable the second receiver of the IMD in response to one of the first and the second differential amplifiers, which is enabled and not being auto-zeroed, detecting a predetermined conductive communication signal within a frequency range.

12. The IMD of claim 11, further comprising:
at least one of a controller, processor and/or clock circuitry configured to generate one or more signals that are provided to the first and the second differential amplifiers to cause, at all times, at least one of the first and the second differential amplifiers to be enabled and not auto-zeroed.

13. The IMD of claim 11, wherein:
the second receiver, while not enabled, draining substantially no current and thus substantially no power from the battery;
the second receiver, while enabled, is configured to receive one or more conductive communication signals within a second frequency range that is higher than the first frequency range, the conductive communication signals transmitted by at least one of a further IMD or an external programmer; and
the second receiver, while enabled, consuming more power than the first receiver.

14. The IMD of claim 11, wherein the first and the second differential amplifiers are simultaneously enabled for less than 20% of a time that only one of the first and the second differential amplifiers is enabled.

15. The IMD of claim 14, wherein one of the first and the second differential amplifiers is being auto-zeroed for at least a majority of a time that the first and the second differential amplifiers are simultaneously enabled.

16. A method for use with an implantable medical device (IMD) comprising first and second electrodes, and a receiver including first and second differential amplifiers, wherein each the first and the second differential amplifiers includes differential inputs and an output, and wherein the first and the second electrodes are electrically coupled to the differential inputs of the first differential amplifier and the differential inputs of the second differential amplifier, and wherein each of the first and the second differential amplifiers is capable of being selectively put in an auto-zero phase while enabled, the method comprising:

providing a same conductive communication signal, that is sensed by the first and the second electrodes, to both the first differential inputs of the first differential amplifier and the second differential inputs of the second differential amplifier;

selectively enabling the first and the second differential amplifiers such that at any given time at least one of the first and the second differential amplifiers is enabled;

selectively putting the first and the second differential amplifiers in an auto-zero phase such that while the first differential amplifier is enabled and in the auto-zero phase the second differential amplifier is enabled without being in the auto-zero phase, and such that while the second differential amplifier is enabled and in the auto-zero phase the first differential amplifier is enabled without being in the auto-zero phase; and always using at least one of the first and the second differential amplifiers to monitor for a predetermined conductive communication signal within a frequency range.

17. The method of claim 16, further comprising:
using at least one of a processor, controller and/or clock circuitry to generate one or more signals that are used to perform the selectively enabling and the selectively putting.

18. The method of claim 16, wherein the selectively enabling is performed such that the first and the second differential amplifiers are simultaneously enabled for less than 20% of a time that only one of the first and the second differential amplifiers is enabled.

19. The method of claim 18, wherein the selectively putting the first and the second differential amplifiers in an auto-zero phase is performed such that one of the first and the second differential amplifiers is being auto-zeroed for at least a majority of a time that the first and the second differential amplifiers are simultaneously enabled.

20. The method of claim 16, wherein the receiver including the first and the second differential amplifiers comprises a first receiver, and wherein the predetermined signal comprises a wakeup signal within a first frequency range, and the method further comprising:

enabling a second receiver in response to the wakeup signal within the first frequency range being detected by one of the first and the second differential amplifiers of the first receiver; and using the second receiver to receive one or more conductive communication signals within a second frequency range that is higher than the first frequency range while the second receiver is enabled;

wherein the second receiver consumes more power than the first receiver while the second receiver is enabled.

* * * * *